United States Patent [19]

Tudoriu

[11] 4,177,805

[45] Dec. 11, 1979

[54] PENILE IMPLANTATION PROSTHESIS

[75] Inventor: Theodor Tudoriu, Munich, Fed. Rep. of Germany

[73] Assignee: Peter Falge, Fed. Rep. of Germany; a part interest

[21] Appl. No.: 854,476

[22] Filed: Nov. 23, 1977

[30] Foreign Application Priority Data

Aug. 12, 1977 [DE] Fed. Rep. of Germany ....... 2736443

[51] Int. Cl.² ............................................. A61F 5/42
[52] U.S. Cl. ..................................................... 128/79
[58] Field of Search ................................. 128/79; 3/1

[56] References Cited

U.S. PATENT DOCUMENTS

| | | | |
|---|---|---|---|
| 3,893,456 | 7/1975 | Small et al. | 128/79 |
| 3,987,789 | 10/1976 | Timm et al. | 128/79 |
| 4,066,073 | 1/1978 | Finney et al. | 128/79 |

Primary Examiner—Lawrence W. Trapp
Attorney, Agent, or Firm—Roylance, Abrams, Berdo & Farley

[57] ABSTRACT

A prosthesis implant particularly for use in a penis has an encasing body in which a stiffening bar is embedded. The implant is bendable in only one direction from its straightened position because of a special bending joint. The joint is formed with slits to permit the unidirectional motion. Various embodiments are disclosed.

11 Claims, 11 Drawing Figures

PENILE IMPLANTATION PROSTHESIS

This invention relates to penile implantation prosthesis.

BACKGROUND OF THE INVENTION

Prosthetic devices for implantation in the penis are intended for use with patients who suffer from the condition known as impotentia coeundi, which is an inability on the part of a male to perform the sexual act. One who suffers from this affliction, which is traceable to various causes, exhibits an inability to achieve a complete state of erection.

The medical literature as well as various patents disclose numerous means for the treatment of this condition. As an example, U.S. Pat. No. 3,893,456, discloses an implantation prosthesis for simulating the state of erection. This prosthesis consists of an elongated relatively rigid bar or rod which is encased in an elongated soft plastic housing. A pair of such bars is constructed such that they may be surgically implanted into the corpora cavernosa areas of the penis, the two columns of erectile tissue on the dorsum of the penis, in order to maintain a lasting state of erection. The implantation of the rigid bodies into the penis does, indeed, cause the desired state of erection, but it can be physically uncomfortable and emotionally irritating.

Another penis implantation prosthesis is shown in German Offenlegungsschriften No. 26 46 323, wherein a stiffening bar completely embedded in an encasing body consists of a metal alloy which is manually bendable. As a result of the implantation of this prosthesis in a penis which otherwise is no longer capable of erection, a state of erection is simulated in regard to the length and thickness of the thickness of the penis. However, the implantation prosthesis does not serve the purpose of lastingly simulating the phallus state and, therefore, the state of erection of the penis, and as a result of that the patient may be emotionally irritated and would feel, at least, physically uncomfortable. Whenever the phallus state is to be achieved, this must take place by manual bending of the particular metallic stiffening bar of the encasing body of the implantation prosthesis. The phallus state is reversed in the same fashion.

BRIEF DESCRIPTION OF THE INVENTION

An object of the present invention is to provide a penis implantation prosthesis of a type which requires no special handling in order to reach or reverse the phallus state. In particular, even after implantation of the prosthesis in accordance with the invention, the penis always assumes the position which belongs to it naturally and not necessarily the phallus state.

Briefly described, the invention includes a penile implantation prosthesis comprising an elongated encasing body formed from a physiologically inert and pliable material, and a stiffening bar completely embedded in said body and extending from the proximal end of said body to a location spaced from the distal end thereof, the stiffening bar being formed from a material more resistant to bending than said body, said body being dimensioned so that it can be surgically inserted into the corpora cavernosa of a penis with the proximal end anchored near the rami of the pubis and distal end in approximately the geometric center of the glans penis, said stiffening bar including a joint portion which is bendable from a substantially straight configuration to a curved configuration in only one direction, said joint portion being located in said body so that, when implanted, it lies along the transition area between the rami of the pubis and the base of the penis shaft.

In order that the manner in which the foregoing and other objects are attained in accordance with the invention can be understood in detail, particularly advantageous embodiments thereof will be described with reference to the accompanying drawings, which form a part of this specification:

Figure 1:
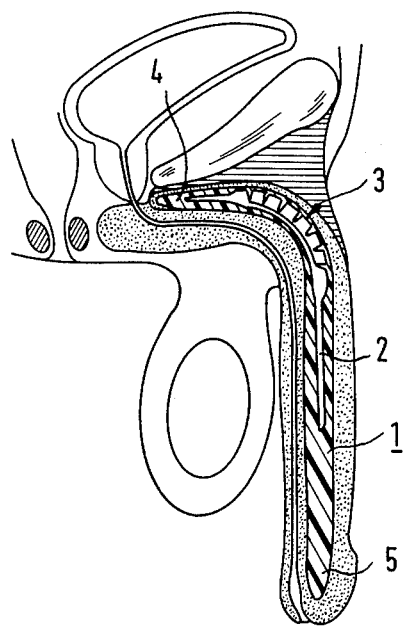
FIG. 1 is a schematic side elevation, in section, of the male anatomy along the longitudinal direction of one of the corpora cavernosa areas of a penis after implantation of a prosthesis in accordance with the invention, the penis being in a semi-erective state as to length and thickness.

As will be recognized from the figures, and from the detailed discussion thereof hereinafter, the prosthesis of the present invention includes a joint which is undirectionally operable, i.e., a joint which can be deflected in one direction only from the elongated or substantially straight condition into a bent condition. Because of this, it is possible when the prosthesis is properly aligned in the surgical implantation process that the prosthesis in the area of the undirectional joint is bent under the force of its own weight and that of the penis downwardly into the normally relaxed position of the penis. Any force acting upwardly on the penis will erect the latter while straightening the joint of the stiffening bar into the phallus position without significantly changing the semi-erective state of the penis as to the length and thickness beyond that achieved by the mere implantation of the prosthetic device. Immediately after relaxing of the erection force stretching the joint of the stiffening bar into the straight position, the joint swings back into its normal position of a bent state.

It has been found that a highly effective joint for this purpose can be formed by providing incisions or slits in the stiffening bar, the slits lying in succession one behind the other, extending transversely across the joint, and essentially in a row in the axial direction or, alternatively, be separate sections arranged in substantially the same manner in the reinforcing bar. When slits are provided in the manner indicated, which slits can be directed either radially transversely or obliquely to the axis of the reinforcing bar, the slits provide the possibility of spreading the area of one side of the reinforcing bar intersected by the slits for the purpose of bending the joint while that portion not having the slits practically represents the hinge of the joint. Whenever, on the other hand, separate segments are provided in the reinforcing bar, then the action is such that the area intersected by the segments can be compressed for the purpose of bending the joint and the area not intersected by the sections represents the hinge of the joint. Notched intersections and sections can be provided at the same time, which characteristic has a favorable effect on the flexibility of the joint, in which case the intersections and the sections should be disposed diametrically opposed to each other. At the same time, a bridge remaining between the intersections on the one hand and the sections on the other hand forms, for practical purposed, a bridging lamella between the adjacent areas of the stiffening bar not interspersed by intersections and segments.

When the stiffening bar is in the stretched or straight condition, and when it is provided with simple interstices, any bending of the joint in the direction opposite the one in which it is intended to be bent will be prevented because the segments or surfaces of the intersections rest on or abut each other and provide a force which resists bending movement beyond that straightened condition.

Whether the joint portion is subdivided by simple intersections, such as slits, or whether it is formed using separate sections, the joint area of the stiffening bar can be made such that areas along the base of the slits or sections are separated from the remaining area of the stiffening bar. The areas thus separated consist of little discs lying one behind the other in an axial direction, similar in form to coplanar lamellae, and the other area opposite can be subdivided by sections in the form of wedge-shaped lamellae, the thinnest area of which is disposed on the outside of the stiffening bar.

The sector of the stiffening bar having the slits or separate sections, referred to as the joint portion, should be approximately 4 centimeters long. With that length, the necessary swiveling range of the prosthesis can be achieved without difficulty, especially when the incisions are separated by axial distances of about 2-4 millimeters, or, alternatively, the separate segments are made having thicknesses in that range.

The number and radial extent of the incisions or the number, the radial extent and the axial extent of the sections, should be dimensions with due consideration of the pertinent portion of the stiffening bar in such a way that the bending is sufficient to achieve an angle between the proximal end of the stiffening bar and the distal portion thereof of at least 90° can be achieved by the joint. Such flexibility can be achieved with the stated characteristics in various ways depending to some degree on the bending strength or resistance of the material used for the stiffening bar.

In order to insure lasting functioning of the joint, the stiffening bar should be thickened in the area of the joint, relative to the remainder of the bar, so that bending of the joint is possible without any danger of breaks of the joint portions thereof.

As a general matter, it should also be noted that the length of the implantation prosthesis of the invention as well as the diameter are to be adapted to the personal physical data of the patient. This is also true for the selection of the material which is the be used in each case, particularly as to its bending strength or hardness. Naturally, in the case of this material, it must be a physiologically inert material. A silicon rubber material is particularly suitable for the encasing body since it is physiologically compatible and also guarantees that no pressure points will develop on the prosthesis which could lead to changes of the surrounding tissue. As material for the stiffening bar, any kind of plastic can be used so long as the selected material can, without any harm to its own quality and existing bending resistance characteristics, be recast within the material used for the encasing body. The material for the stiffening bar should be of greater bending resistance, because of its special function, than the material for the encasing body.

Figure 2:
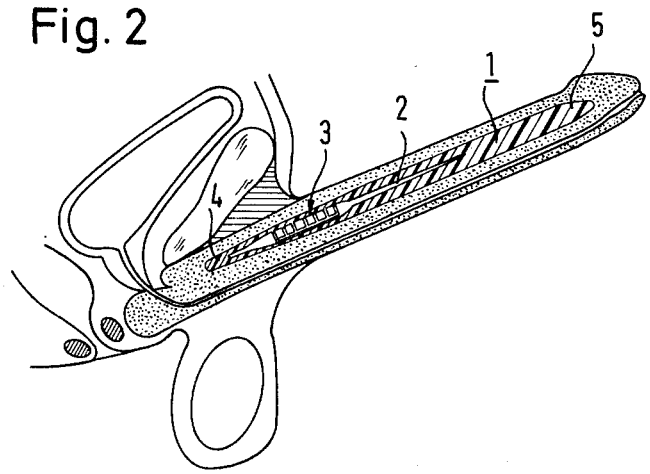
FIG. 2 is a side elevation, in partial section, similar to FIG. 1 and showing the penis in phallus position.

Referring now to the drawings, it will be seen in the schematic anatomical illustration of FIG. 1, that the penis shown therein is in a quasi-erective state, and the implanted prosthesis 1 is bent downwardly, the bend therein occurring in the area of the joint 3 provided in the stiffening bar 2. In FIG. 2, however, the penis is shown in the true phallus position, wherein the joint 3 of the stiffening bar 2 of the prosthesis is straightened out. At the same time, FIG. 2 clearly shows that the proximal end 4 of the prosthesis is inserted and anchored in the area of the rami of the pubis, while the distal end 5 lies in the area of the geometrical center of the glans penis.

Figure 3:
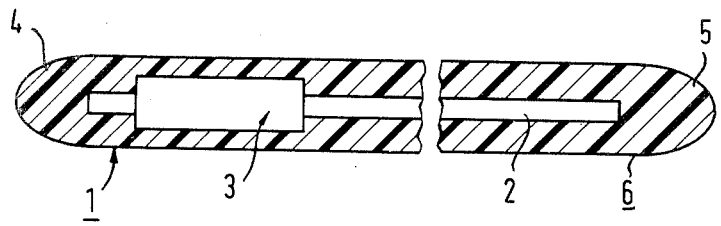
FIG. 3 is an enlarged longitudinal section through the encasing body of a prosthesis in accordance with the invention.

FIG. 3 shows the prosthesis itself, viewed in longitudinal section. As will be seen, the device includes a stiffening bar 2 with a unidirectional joint portion 3. The stiffening bar or rod is preferably of a cylindrical shape, and the bar with its joint 3 is completely surrounded by an encasing body 6 which is also a cylindrical elongated body having rounded ends. The material of the encasing body is pliable and is more pliable than the stiffening bar 3. The joint 3 is, of course, shown in FIG. 3 only in outline.

Various embodiments of the joint are shown in FIGS. 4–11, enlarged and apart from the encasing body. In each of these detailed illustrations, provision has been made that the portion of stiffening bar 2 to be equipped with joint 3 is made larger in diameter and is strengthened as compared to the remaining area of the stiffening rod 2. Such reinforcement is desirable but is not absolutely necessary.

Figure 4:
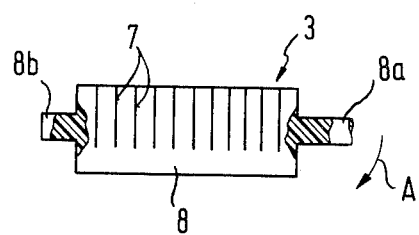
FIGS. 4–10 are side elevations, in partial section, of the joint portion of stiffening bars placeable in the encasing body of FIG. 3.

FIG. 4 shows an embodiment of the unidirectional joint which is formed such that the enlarged diameter region is provided with a plurality of simple transverse incisions or slits 7 which extend over a portion of the diameter of the joint and lie axially one behind the other, the slits thus being parallel and extending transversely with respect to the longitudinal axis of the bar. The two portions 8a and 8b of stiffening bar 2 are connected with one another through an area 8 which does not have the slits and thus forms a lamella bridging slits 7. The joint 3 of FIG. 4 is bendable in the direction of arrow A from the straightened position shown so that the lamella 8 forms, in a manner of speaking, the hinge joint.

Figure 5:
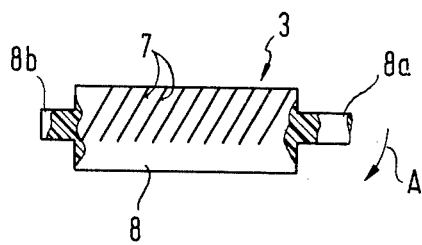

FIG. 5 shows an embodiment somewhat similar to FIG. 4, but wherein the slits do not lie in planes perpendicular to the longitudinal axis of bar 2, but, instead, extend at an oblique angle to that axis on the order of 30°. The action of the joint of FIG. 5 is similar to that of FIG. 4.

Figure 6:
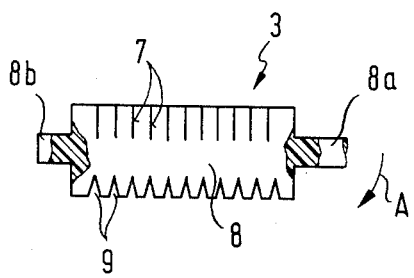

FIG. 6 illustrates another embodiment in which the slits 7 do not extend as deeply as the slits in the embodiments of FIGS. 4 and 5, and the joint is further provided with inwardly extending cut-outs or notches 9 which are diametrically opposite slits 7. The notches are wedge-shaped and taper inwardly toward the central axis of the bar. The continuous lamella portion 8 extends longitudinally between slits 7 and notches 9 and again interconnects the portions 8a and 8b of the stiffening bar, bridging the slits 7 and notches 9.

Figure 7:
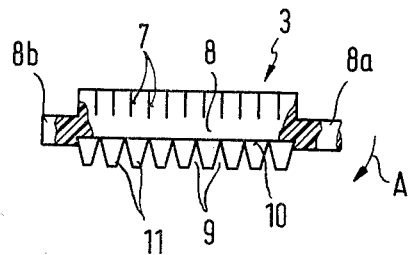

Yet another embodiment is shown in FIG. 7 which is somewhat similar to FIG. 6, but wherein that portion of joint 3 provided with notches 9 is formed as a separate piece inserted into a recess 10. It will be observed that the line 10 forming the base of the recess extends through the base of the notches 9 so that successive lamellae 11 are formed by means of the notches.

Figure 8:
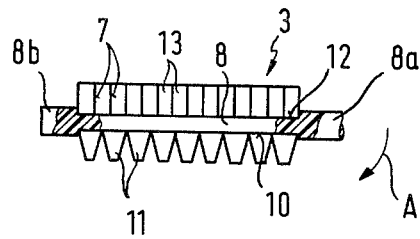

A still further embodiment is shown in FIG. 8 in which not only the portion having the notches but also the portion having slits 7 are formed as separte pieces. In this embodiment, the slits extend to the surface 12, forming coplanar lamellae 13 between slits 7, the portion lying between surfaces 10 and 12 again forming the lamella interconnecting the end portions of the stiffening bar.

Figure 9:
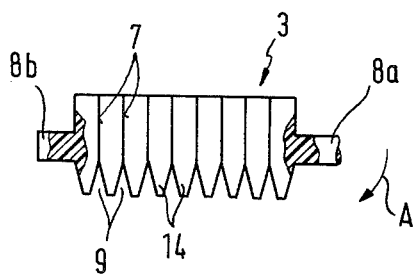

In the embodiment of FIG. 9, the incisions 7 are formed such that they extend entirely through the joint portion, each of slits 7 intersecting the apex of one of notches 9, thereby forming a plurality of parallel lamellae 14, all of which are of substantially the same shape. In this embodiment, there is no continuous portion 8 extending between the end portions 8a and 8b of the stiffening bar 2. However, this is not a disadvantage in view of the action of the joint which is an object of the invention, since the entire stiffening bar 2 including joint 3 is completely embedded in the encasing body 6, which body prevents any lateral relative slippage of the lamellae relative to each other. It will be noted that the end ones of the lamellae are fixedly attached to the end portions 8a and 8b of the stiffening bar, respectively.

Figure 10:
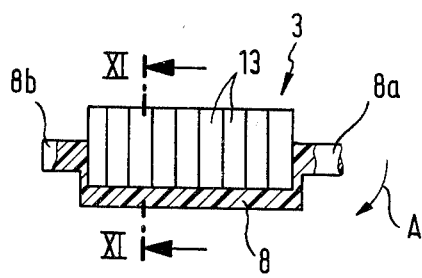
Figure 11:
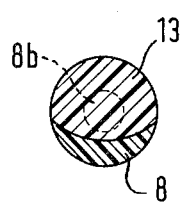
FIG. 11 is a transverse section along lines XI—XI of FIG. 10.

Yet another embodiment is shown in FIG. 10, wherein the areas 8a and 8b of the stiffening bar are again connected to a continuous longitudinal lamella 8, which has a special shape broadly resembling the letter U. The end portions and portion 8 together form a recess to receive a plurality of coplanar lamellae 13 which correspond in circumferential shape to the shaping of the circumference of the overall joint, taken together with lamella 8, so that the entire assembly forms a body, in the straight position, having a cylindrical outer surface. It will be observed that the undirectional operable joint shown and described in connection with the foregoing description and drawings in various embodiments may have uses other than as an implantation prosthesis. The joint is suitable for use in other applications where it is desirable to provide a joint which permits movement between a straight position and a curved condition in only one direction from the straight position and which, concurrently, prevents bending in the opposite direction beyond the straightened state.

While certain advantageous embodiments have been chosen to illustrate the invention, it will be understood by those skilled in the art that various changes and modifications can be made therein without departing from the scope of the invention as defined in the appended claims.

What is claimed is:

1. A penile implantation prosthesis comprising
   an elongated encasing body formed from a physiologically inert and pliable material, and
   a stiffening bar completely embedded in said body and extending from the proximal end of said body to a location spaced from the distal end thereof, said stiffening bar being formed from a material more resistant to bending than said body,
   said body being dimensioned so that it can be surgically inserted into the corpora cavernosa of a penis with the proximal end anchored near the rami of the pubis and the distal end in approximately the geometric center of the glans penis,
   said stiffening bar including a joint portion which is bendable from a substantially straight configuration to a curved configuration in only one direction, said joint portion being located in said body so that, upon implantation, said joint portion resides along the transition area between the rami of the pubis and the base of the penis shaft.

2. A prosthesis according to claim 1 wherein said joint portion includes means defining a plurality of substantially parallel slits in said joint portion of said bar, said slits extending transversely across said bar to form a plurality of adjacent segments.

3. A prosthesis according to claim 2 wherein said segments are joined to each other along one side by a portion of said bar.

4. A prosthesis according to claim 2 wherein said joint portion includes means defining a plurality of notches extending inwardly into a side of said bar opposite said slits, said notches being arranged longitudinally along said portion.

5. A prosthesis according to claim 4 wherein said notches taper inwardly toward a central axis of said bar.

6. A prosthesis according to claim 4 wherein a continuous portion of said bar separates said slits from said notches.

7. A prosthesis according to claim 6 wherein each of said notches lies transversely across said continuous portion from one of said slits.

8. A prosthesis according to claim 4 wherein the axial length of said joint portion having said slits and notches is about 4 centimeters.

9. A prosthesis according to claim 4 wherein said slits and notches are dimensioned relative to the thickness of said bar so that said bar is bendable to form an angle between the proximal and distal ends thereof of about 90°.

10. A prosthesis according to claim 9 wherein the joint portion of said bar is thicker than the remainder of said bar.

11. A prosthesis according to claim 1 wherein said joint portion includes means defining a plurality of notches extending inwardly into only one side of said bar.

* * * * *